(12) United States Patent
Franck

(10) Patent No.: US 6,925,332 B2
(45) Date of Patent: Aug. 2, 2005

(54) METHODS FOR PROGRAMMING A NEURAL PROSTHESIS

(75) Inventor: Kevin H. Franck, Bala Cynwyd, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 160 days.

(21) Appl. No.: 10/356,524

(22) Filed: Feb. 3, 2003

(65) Prior Publication Data

US 2004/0152946 A1 Aug. 5, 2004

(51) Int. Cl.$^7$ ................................................ A61N 1/36
(52) U.S. Cl. ........................................... 607/57; 600/25
(58) Field of Search ....................... 600/25; 607/55–57; 73/585; 381/314, 315

(56) References Cited

U.S. PATENT DOCUMENTS

| | | |
|---|---|---|
| 3,751,605 A | 8/1973 | Michelson |
| 4,267,410 A | 5/1981 | Forster et al. |
| 4,284,856 A | 8/1981 | Hochmair et al. |
| 4,357,497 A | 11/1982 | Hochmair et al. |
| 4,400,590 A | 8/1983 | Michelson |
| 4,408,608 A | 10/1983 | Daly et al. |
| 4,428,377 A | 1/1984 | Zollner et al. |
| 4,532,930 A | 8/1985 | Crosby et al. |
| 4,577,641 A * | 3/1986 | Hochmair et al. .......... 600/559 |
| 5,626,629 A | 5/1997 | Faltys et al. |
| 6,157,861 A | 12/2000 | Faltys et al. |
| 6,609,032 B1 * | 8/2003 | Woods et al. ................. 607/46 |

* cited by examiner

Primary Examiner—John P. Lacyk
(74) Attorney, Agent, or Firm—Caesar, Rivise, Bernstein, Cohen & Pokotilow, Ltd.

(57) ABSTRACT

This invention relates to methods for programming a neural prosthesis, more particularly to methods for programming a hearing prosthesis, and most particularly to methods for fitting a speech processor and implantable cochlear stimulator by programming the speech processor.

24 Claims, 4 Drawing Sheets

METHODS FOR PROGRAMMING A NEURAL PROSTHESIS

BACKGROUND OF THE INVENTION

1. Field of Invention

The inventive subject matter relates to methods for programming a neural prosthesis, more particularly to methods for programming a hearing prosthesis, and most particularly to methods for fitting a speech processor and implantable cochlear stimulator by programming the speech processor.

2. Background

Hundreds of disorders affect the nervous system. Some, like stroke, the epilepsies, and Alzheimer's disease and other effects of aging, affect millions of Americans. Many neurological disorders produce a loss of function in motor and/or sensory nerve pathways, resulting in a variety of disabilities in humans. An important part of the effort to restore function in neurologically disabled individuals is the use of neural prosthetics. Neural prostheses are electronic and mechanical devices that connect with the nervous system to restore lost function. Such devices generally include electrodes that interface with biological tissue, a power and telemetry receiver, control electronics, and a biocompatible package for the implanted electronics.

Present devices afford some restoration of function in relation to their biological counterparts, but research is ongoing to improve the function of these devices. The Neural Prosthesis Program at the National Institute of Neurological Disorders and Stroke of the National Institutes of Health supports the development of implants for the purpose of forming in-going and out-going connections with the nervous system, which are needed for the development of neural prostheses for individuals with sensory and motor disabilities. Prosthetic devices for all the five major senses—hearing, sight, touch, taste, and smell—are under development. With the ongoing development of more sophisticated and sensitive devices, the need for the effective programming or fitting of a device to an individual is expected to increase. A goal of the inventive subject matter is to contribute to the overall process of reducing the burden of neurological disorders by providing methods for the improved, user-directed programming or fitting of a neural prosthesis, particularly a hearing prosthesis, and most particularly to a cochlear implant or other implantable hearing prosthesis having a speech processor.

An exemplary class of sensorineural prosthetic devices are the hearing prostheses. Types of hearing prostheses include simple sound amplification devices such as the traditional hearing aid; more sophisticated sound amplification devices which are adjustable to the specific deficiencies in a user's hearing profile; and implantable devices such as cochlear implants and cortical implants, which bypass the organic hearing mechanism and directly stimulate the sensory nerves and/or brain centers of hearing, to replicate the ability to perceive sound. Other sensorineural prosthetics currently under development include vision prostheses, tactile sensation prostheses, olfactory prostheses, and gustatory prostheses.

Cochlear prostheses produce sensations of sound in deaf patients by direct electrical stimulation of the auditory nerve. In modern, multichannel cochlear prostheses, several different sites are stimulated at various distances along the cochlea to evoke the different pitches of sound perception that are normally encoded by nerve activity originating from the respective sites. The patterns of electrical stimulation are derived from acoustic signals picked up by a microphone and transformed by a speech processor that is programmed to meet the particular requirements of each patient.

Several different schemes for processing the acoustic signal and transforming it into electrical stimuli have been developed; see U.S. Pat. No. 3,751,605 (Michelson); U.S. Pat. No. 4,400,590 (Michelson); U.S. Pat. No. 4,267,410 (Forster et al.); U.S. Pat. No. 4,284,856 (Hochmair et al.); U.S. Pat. No. 4,408,608 (Daly et al.); U.S. Pat. No. 4,428,377 (Zollner et al.); and U.S. Pat. No. 4,532,930 (Crosby et al.). All such stimulators generate electrical stimulation pulses that may be selectively applied to the cochlea of a patient through an appropriate electrode or electrode array. Thus, U.S. Pat. Nos. 4,284,856 and 4,357,497 disclose a sound processor including multiple channel signal transmission to a subcutaneously implanted receiver for selectively stimulating the cochlea through electrodes in an implanted prosthesis.

The totally deaf or severely hearing impaired user of such implanted devices presents a special difficulty in fitting a speech processor. The middle or inner ear may be totally non-responsive to sound waves, but the auditory nerve generally can be electrically stimulated to transmit signals to the brain. Thus, in U.S. Pat. No. 4,284,856 the necessity of isoloudness frequency adjustment and dynamic range compression for the wearer of a cochlear prostheses have been disclosed. Establishing proper sound response characteristics of the auditory nerve in such patients is more critical and difficult than is the auditory response of a less severely impaired person. In the latter case, it is conventional to merely establish frequency response of the hearing device which matches the patient's dynamic range, based on an audiogram or other testing.

Thus, one of the more perplexing problems facing users of Cochlear implant systems, and the clinicians and physicians who implant and adjust such systems, is properly setting the stimulation parameters used by these systems. That is, each Cochlear implant system must be adjusted to fit an individual patient, so that sounds are properly perceived by that patient, and so that sounds are not painfully too loud, nor undetectably too soft, nor otherwise unintelligible by the patient.

As the art of cochlear stimulation has advanced, both the implanted portion of the cochlear stimulation system, and the externally wearable speech processor have become increasingly complicated and sophisticated. The amount of control and discretion exercisable by an audiologist in selecting the modes and methods of operation of the cochlear stimulation system have increased dramatically. It is no longer possible to fully control and customize the operation of the cochlear stimulation system through the use of, for example, switches located on the speech processor. As a result, it has become necessary to utilize an implantable cochlear stimulator fitting system to establish the operating modes and methods of the cochlear stimulation system and then to download such programming into the speech processor.

Currently, cochlear implants are fit within a clinical fitting environment where a clinician controls software to produce settings that, in turn, control the device. A clinician then tests the patient in an artificial listening environment with subjective materials, often highly subjective, and often with differing presentation levels, tester voices, etc.

Properly programming an implanted device is especially difficult because heretofore much of what is deemed a proper setting has been a determination made by the clinician, based on feedback from the patient. For example, U.S. Pat. No. 5,626,629 provides a clinician with various adjustment tools, including the use of a personal computer having a special software program loaded therein, that help the clinician set and adjust numerous stimulation parameters. However, due to the age, disability, or other limitations of the patient, often the patient is ineffective at accurately communicating what he or she senses or "hears" through the implant system to the attending medical personnel.

Others have attempted to overcome this lack of effective patient/clinician communication by removing patient feedback from the process. U.S. Pat. No. 6,157,861 discloses an implantable cochlear stimulator (ICS) and a method for fitting the ICS to a particular patient using objective feedback rather than subjective feedback. Such methods commonly rely upon measurements of the stapedius reflex response and the middle ear reflex to objectively measure physiological response to sound.

However, reliance on technology and/or objective measurements often does not provide a patient with a device fully optimized for helping the patient hear common sounds, such as voices, in real-world environments. Currently available systems for programming or fitting of cochlear stimulation systems, while providing a degree of flexibility in the programming of the modes and methods of operation of the cochlear stimulation system based solely or in part of objective measurements taken from the patient, lack the ability to fully integrate subjective patient observations as to the effectiveness of the hearing prosthesis.

Thus, there is a need in the neural stimulation art for techniques, methods, and systems for more accurately fitting a neural prosthesis to the individual patient. The complex biophysical phenomena associated with the electrical excitation of neurons and psychophysical phenomena regarding the interpretation of neural activity by the nervous system suggest that the quality and intelligibility of neural prostheses may be improved in a given patient by more specific manipulations of the electrical stimulus tailored to that patient.

The need for such a system becomes increasingly important with a decease in the age of the patient into which the neural stimulator, such as an implantable cochlear stimulator, is implanted. This is because very young patients, for example two year olds, are unable to provide adequate subjective feedback to the clinician programming the device to accurately fit the neural stimulation system optimally for the patient. Further, currently available programming units do not provide a level of feedback to the audiologist that enables the audiologist to independently evaluate the stimulation being applied to the patient, and thereby optimize such stimulation. Thus, what is needed is an improved apparatus and method for programming a speech processor of a neural stimulation system that provides for the efficient and effective utilization of subjective patient responses in the setting of the modes and methods of operation of the cochlear stimulation system.

Accordingly, an object of the invention is an improved method for fitting a neural prosthesis to a sensorineural-impaired person. Another object of the invention is an improved method for fitting a hearing prosthesis to a hearing impaired person. A further object of the invention is an improved method for fitting a sound processor driving a subcutaneously implanted receiver and prosthetic electrical structure to a severely hearing impaired person. A further object of the invention is an improved method for checking the fitting of a neural prosthesis to the needs of a user.

The inventive subject matter provides improved techniques for programming a neural prosthesis, more particularly a hearing prosthesis, and most particularly for programming an implanted hearing prosthesis such as a Cochlear implant system. The inventive subject matter allows the user of a neural prosthetic device to interface with fitting software directly without the intervention of a clinician. The process includes a video-game based graphical user interface, which is particularly effective with children. The inventive subject matter also includes software having a verification portion that tests a user's abilities with various settings to help the user maximize his or her abilities. The method is particularly advantageous with totally deaf and severely hearing impaired individuals, but the process has applicability to other hearing impaired persons requiring a hearing prosthesis and to other sensorineural-impaired persons requiring a neural prosthesis.

The inventive subject matter solves a number of problems. First, it removes the clinician from the process of relaying a user's perceptual information to the software. Second, with the use of an optional single presentation system in which electrical signals are directly input into the prosthesis, it reduces verification testing variability by eliminating the inherent errors, noise, and other interference which may be found in ambient testing room environments. Third, it eliminates or substantially reduces the clinician's time commitment to device fitting. Fourth, processor settings are optionally set by the user at home, eliminating the need for a clinic visit and associated travel by the user and/or the user's family members.

SUMMARY OF THE INVENTION

The inventive subject matter relates to a method for user-directed fitting of a neural prosthesis to a sensorineural-impaired user, comprising the steps of:

a) connecting a neural prosthesis to the user;

b) connecting an external device for user-directed fitting of a neural prosthesis to said neural prosthesis, for providing a test neural stimulus to said user and receiving a user response;

c) presenting one or more neural stimuli to said user through said neural prosthesis, each said neural stimulus having an associated icon displayed by a user interface connected to said device,
  wherein said associated icon(s) is/are displayed on a first display scene of said user interface, and
  wherein each of said neural stimuli is presented to said user to test for a user response to said neural stimulus;

d) obtaining said user response by monitoring user selection of the associated icon subjectively corresponding to a user-selected neural stimulus; and e) adjusting said neural prosthesis so that the user is enabled to optimally detect said neural stimuli.

In another embodiment, the inventive subject matter relates to a method for user-directed fitting of a hearing prosthesis to a hearing-impaired user, comprising the steps of:

a) connecting a hearing prosthesis to the user;

b) connecting an external device for user-directed fitting of a sound prosthesis to said hearing prosthesis, for providing a test sound stimulus to said user and receiving a user response;

c) presenting one or more sound stimuli to said user through said hearing prosthesis, each said sound stimulus having an associated icon displayed by a user interface connected to said device,
wherein each of said sound stimuli is presented to said user to test for a user response to said sound stimulus using a stimulus threshold perception test, a stimulus discrimination test, or a stimulus recognition test;
d) obtaining said user response by monitoring user selection of the associated icon subjectively corresponding to a user-selected sound stimulus; and
e) adjusting said hearing prosthesis so that the user is enabled to optimally detect said sound stimuli.

In an additional embodiment, the inventive subject matter most particularly relates to a method for user-directed fitting of a hearing prosthesis to a hearing-impaired user, comprising the steps of:
a) connecting a hearing prosthesis to the user;
b) connecting an external device for user-directed fitting of a hearing prosthesis, having a graphical user interface, to said hearing prosthesis for providing a test sound stimulus to said user and receiving a user response;
c) presenting at least three sound stimuli to said user through said hearing prosthesis, each said sound stimulus having an associated animation icon displayed by said graphical user interface,
wherein at least two of the sound stimuli are identical and at least one sound stimulus is different from the identical sound stimuli;
d) obtaining said user response by monitoring user selection of the associated animation icon subjectively corresponding to a user-selected sound stimulus which differs from the identical sound stimuli;
e) providing visual feedback for correct and incorrect responses, displayed to the user within a plurality of display scenes of said graphical user interface; and
f) adjusting said neural prosthesis so that the user is enabled to optimally detect said differing sound stimulus from the identical sound stimuli,
wherein the steps of presenting sound stimuli to the user, determining user response, providing visual feedback, and adjusting the hearing prosthesis are executed by a computer software program.

Additionally, the present invention relates to an apparatus for user-directed fitting of a neural prosthesis to a sensorineural-impaired user, comprising:
a) an input device;
b) a computer processor;
c) a memory device;
d) an information storage and retrieval device;
e) a graphical user interface output device; and
f) a set of computer-readable instructions for processing input and generating output, comprising the steps of:
  i) presenting a neural stimulus to a user through a neural prosthesis, each said neural stimulus having an associated animation icon displayed by said graphical user interface;
  ii) obtaining a user response to said neural stimulus by monitoring user selection of the associated animation icon subjectively corresponding to a user-selected neural stimulus;
  iii) providing visual feedback for correct and incorrect responses, displayed to the user within a plurality of display scenes of said graphical user interface; and
  iv) adjusting said neural prosthesis so that the user is enabled to optimally detect said neural stimulus.

BRIEF DESCRIPTION OF THE DRAWINGS

FIG. 1(a) is a graphic which depicts a simple shape scene for the lowest level of user sophistication. FIG. 1(b) is a graphic which depicts a balloon scene for the lowest level of user sophistication. FIG. 1(c) is a graphic which depicts a frog scene for an intermediate level of user sophistication. FIG. 1(d) is a graphic which depicts a cat scene for an intermediate level of user sophistication. FIG. 1(e) is a graphic which depicts a fishing scene for the highest level of user sophistication. FIG. 1(f) is a graphic which depicts a Godzilla scene for the highest level of user sophistication.

DETAILED DESCRIPTION OF THE INVENTION

Definitions

Figure 1:
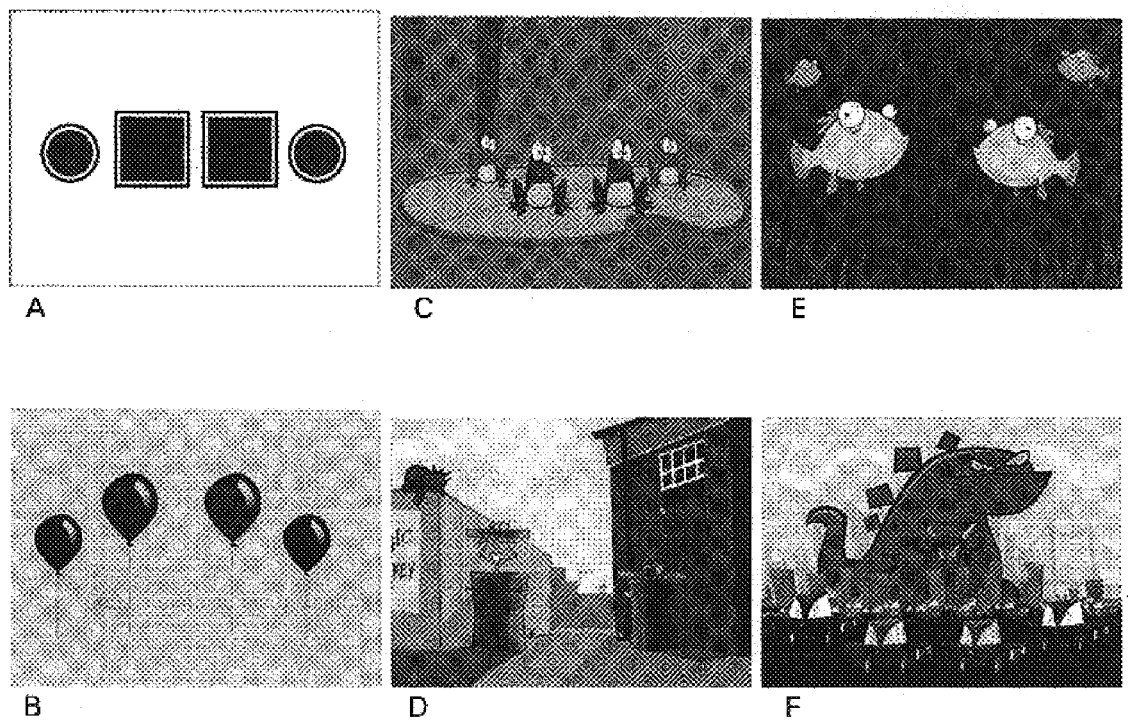
FIGS. 1(a)–(f) are graphics which depict test screen shots for the six scenes comprising three levels of patient sophistication to be used in the graphical user interface of the inventive subject matter.
Figure 2:
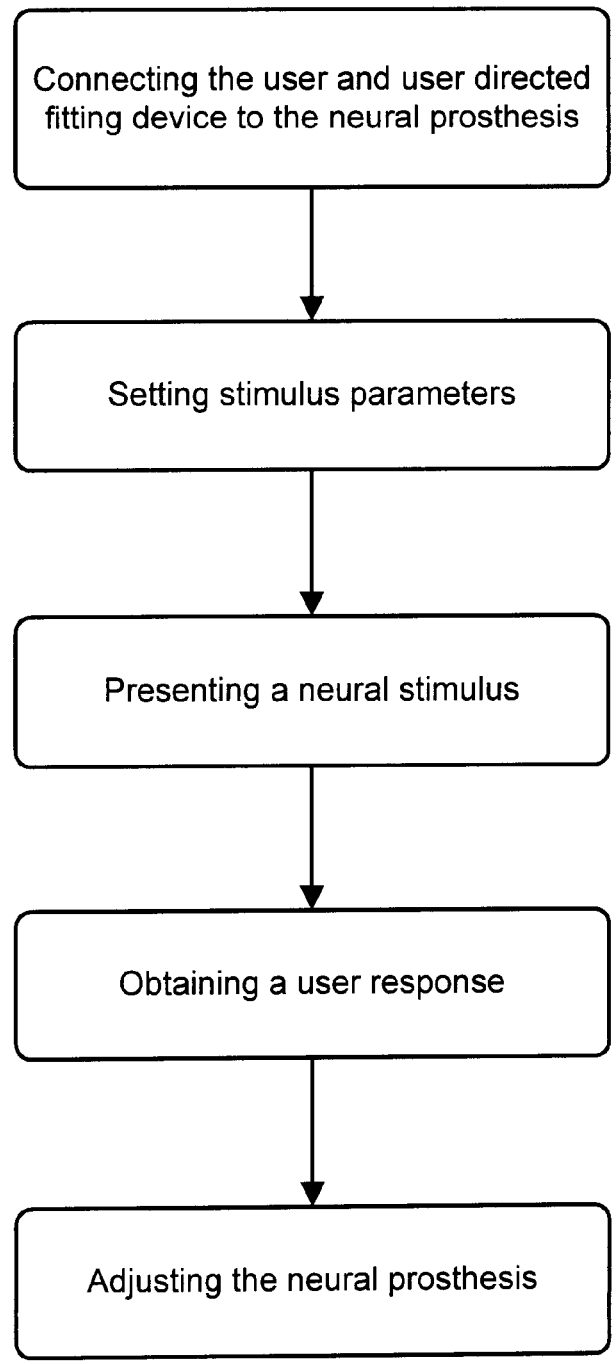
FIG. 2 is a flowchart depicting the steps traversed in order to program a neural prosthesis according to one embodiment of the inventive subject matter.
Figure 3:
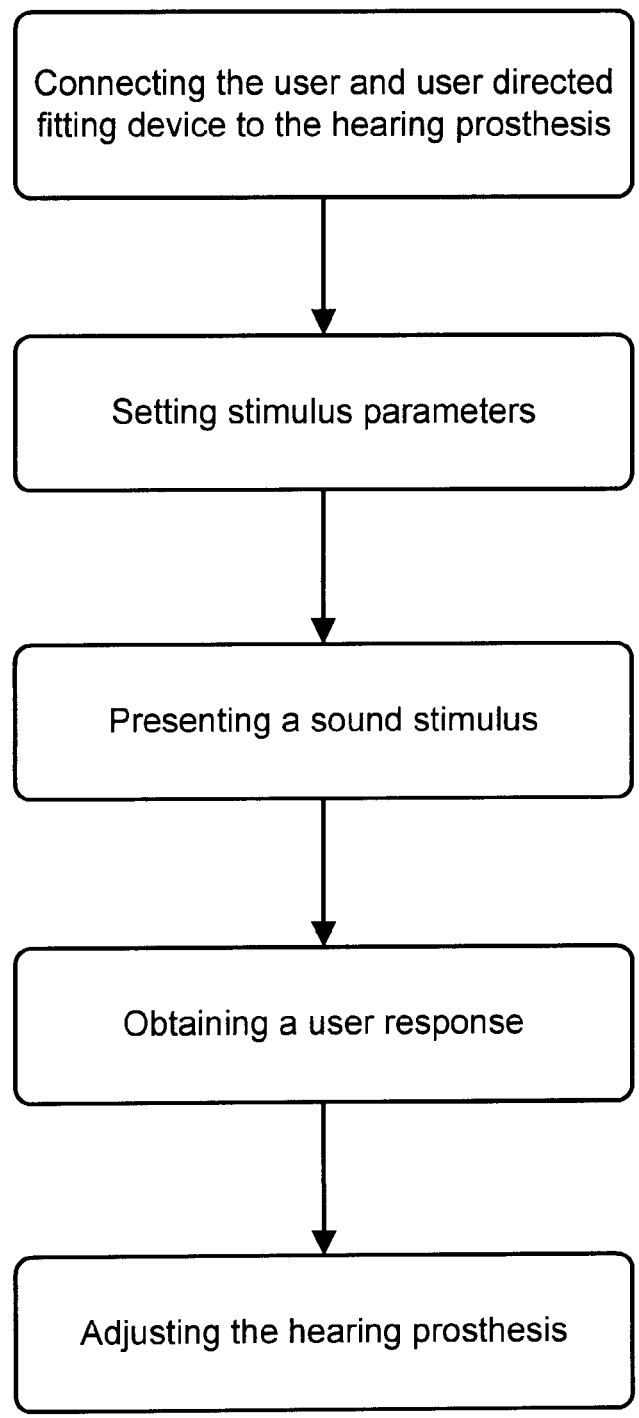
FIG. 3 is a flowchart depicting the steps traversed in order to program a hearing prosthesis according to another embodiment of the inventive subject matter.
Figure 4:
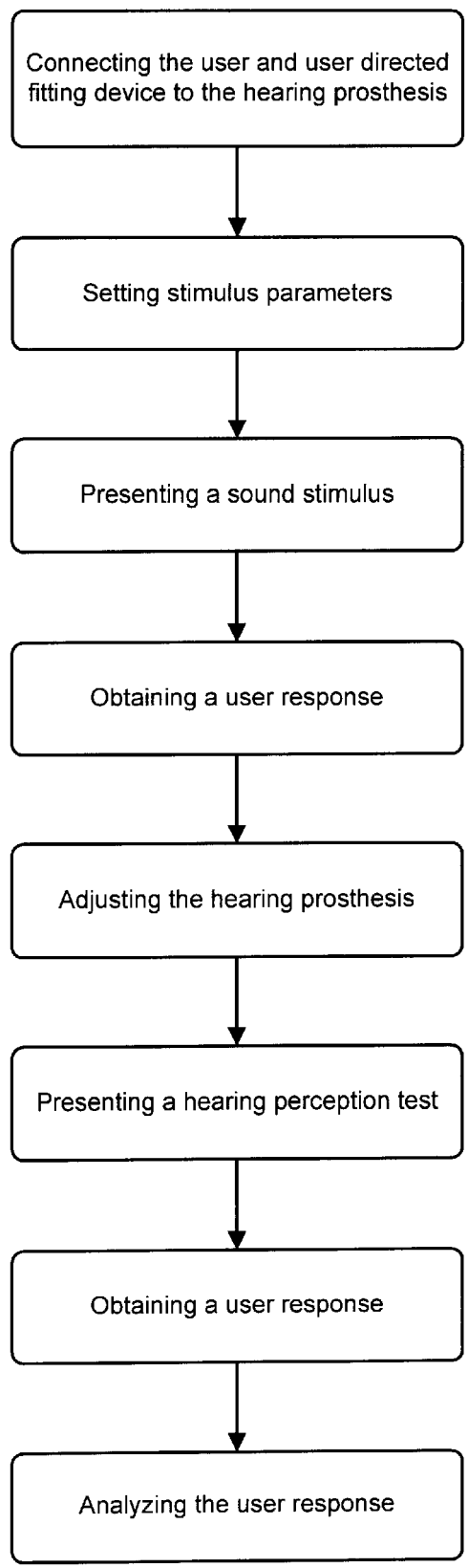
FIG. 4 is a flowchart depicting the steps traversed in order to program a hearing prosthesis according to another embodiment of the inventive subject matter.

"Aided Threshold" refers to the input level at which the patient's threshold when wearing a prosthesis is reached.

"Amplitude Compression" refers to the reduction of the large input signal amplitude range to a lower response range.

"Audio Band" refers to the whole or a part of frequencies between a lower audio frequency and an upper audio frequency, typically between the range of 17 Hz and 17 kHz for normal human hearing.

"Channel", as used herein in relation to neural signal processors, refers to a selected pair of electrodes capable of applying a given neural stimulus to a desired location; in the case of a hearing stimulus, the desired location is within the cochlea.

"Cochlear prosthesis" or "cochlear implant" refers to a device which generates electric signals and delivers them to the auditory nerve via an implanted stimulation electrode, thus causing neural stimulation. The cochlear prosthesis essentially consists of a sound processor, a transmitter for transcutaneous signal transmission, an implanted receiver/stimulator circuitry, and an implanted single or multiple channel stimulating electrode. Instead of a transmitter and receiver, a percutaneous plug is optionally used in some devices. The sound processor can contain one or several channels of sound processing. The number of sound processing channels can be smaller, equal, or greater than the number of stimulating electrodes used.

"Comfort Level" refers to a stimulation level on a single channel that is perceived as comfortable to the patient; in the case of a hearing stimulus, the stimulation level relates to sound loudness.

"Computer system" refers to a conventional computer, for example a standalone personal computer or a workstation of a computer network, which comprises an input device, a computer processor, a memory device, an information storage and retrieval device, a set of computer-readable instructions for processing input and generating output, and an output device. As one of ordinary skill in the art will readily understand, the selection of the hardware components of a computer system, as well as the quantity and parameters of the selected components, is one of convenience in constructing the computer system to the requirements of the user. Computer systems are commercially available and well known in the art.

"Dynamic Range" refers to the range between Electrical Threshold and Comfort Level. Sound intensity dynamic range is the range in which input sound intensities are mapped into the electrical dynamic range.

"Electrical Threshold" refers to the minimum electrical stimulation level that can be perceived by the patient in a given channel of the neural prosthesis.

"Fitting" refers to the process of customizing a prosthesis to a patient by setting the appropriate psychophysical parameters to a level or setting that is both effective in allowing the prosthesis to optimally perform its intended function and comfortable for the patient.

"ICS" refers to an Implantable Cochlear Stimulator, including an electrode array having spaced-apart electrodes adapted for insertion into the cochlea. The ICS typically includes multiple channels, each of which may provide neural stimuli to a selected pair of the spaced-apart electrodes, called bipolar stimulation, and/or to a selected one of the spaced-apart electrodes and a reference electrode, called monopolar stimulation. Each channel thus effectively delivers a neural stimulus to a different section or location of the cochlea.

"Middle Ear Reflex" or "MER" refers to mechanical tension produced by the stapedius and tensor tympani, two muscles of the middle ear, in response to neural signals received from the brain.

"Most Comfortable Loudness" or "MCL" refers to the level for best intelligibility or comprehension and, in the case of a hearing stimulus, to which one could comfortably listen for an extended period of time.

"Neural prosthesis" refers to an artificial device added to the human body to replace or supplement the function of a sensory or motor nerve that is missing or damaged. Thus, "hearing prosthesis" refers to a device, such as a hearing aid or cochlear implant, which replaces or supplements the sense of hearing. Similarly, without limiting the scope of the claims herein, "vision prosthesis" for example refers to both internal and external prescription lenses, and multi-channel retinal neurostimulators which comprise an externally worn transmitter and a body implantable stimulator; "tactile sensation prosthesis" for example refers to tactile transducers and related brain implants; "olfactory prosthesis" for example refers to detectors incorporating expressed olfactory receptor proteins, and related brain implants; "gustatory prosthesis" for example refers to detectors incorporating expressed gustatory receptor proteins, and related brain implants, and "motor prosthesis" for example refers to motor cortex implants for the generation of motor output.

"Neural stimulus" refers broadly to any real or artificial stimulation which leads to excitation of a tissue or cell of the nervous system. Non-limiting examples of neural stimuli include environmental stimuli such as sound, light, contact with physical objects, and taste and smell events triggered by inhalation or ingestion of materials, as well as artificially produced stimuli such as electrical potentials applied to neural tissue.

"Psychophysic" refers to the relationship between physical stimuli and sensory response.

"Sensorineural" refers to a characteristic of, relating to, or involving the sensory nerves. "Sensorineural-impaired" refers broadly to any impairment of the sensory nerves, including, but not limited to, impairments of hearing, vision, touch, smell, and taste.

"Sound" refers to acoustic vibrations transmitted through an elastic solid, liquid, or gas which are within the frequency and amplitude ranges capable of being detected by human organs of hearing, generated either acoustically or as an electric waveform which is supplied to an implanted electrode to replicate the effect of acoustic vibrations detected by human organs of hearing. As used in the claims herein, "a sound" refers to both simple sounds, such as pure tones, and complex sounds, such as music or multiple simultaneous conversations.

"Speech processor" and "sound processor" refer to a device that senses audio sounds, converts such sounds to electrical signals, and processes the electrical signals in accordance with a prescribed speech processing strategy to produce stimulation control signals.

"Stapedius Reflex Response" refers to Contraction of the stapedius muscle. Such response occurs when the patient is exposed to an electrical stimulation level of between about 70–100 dB equivalent sensation level. As is known in the art, this response may be used to estimate comfortably loud levels for the patient.

"Test for neural perception" refers to a controlled test for the correct perception and identification of known information by the senses. Such test may be directed to the perception of a minimum threshold, referred to herein as a "stimulus threshold perception test"; determination of a maximum threshold; discrimination between stimuli, referred to herein as a "stimulus discrimination test"; or recognition and identification of a particular stimulus, referred to herein as a "stimulus recognition test". Non-limiting examples of neural perception tests include "hearing perception tests" such as audiograms, standard speech perception tests, and consonant and vowel confusion tests; eye charts and other visual acuity tests, object recognition tests, color recognition tests, contrast sensitivity tests, scent recognition tests, tactile recognition tests, and the like.

"Threshold" refers to the level at which a neural stimulus becomes detectable. "Threshold of hearing" refers to the level of sound stimulation which can be perceived or heard.

METHODS OF THE INVENTION

Present prosthetic devices afford some restoration of function in relation to their biological counterparts, but research is ongoing to improve the function of these devices. With the development of more sophisticated and sensitive devices, the need for the effective programming or fitting of a device to an individual is expected to increase. A goal of the inventive subject matter is to contribute to the overall process of reducing the burden of neurological disorders by providing methods for the improved, user-directed programming or fitting of a neural prosthesis. Exemplary sensorineural prosthetics include hearing prostheses, vision prostheses, tactile sensation prostheses, olfactory prostheses, and gustatory prostheses.

Thus, the inventive subject matter relates to a method for user-directed fitting of a neural prosthesis to a sensorineural-impaired user, comprising the steps of:

a) connecting a neural prosthesis to the user;

b) connecting an external device for user-directed fitting of a neural prosthesis to said neural prosthesis, for providing a test neural stimulus to said user and receiving a user response;

c) presenting one or more neural stimuli to said user through said neural prosthesis, each said neural stimulus having an associated icon displayed by a user interface connected to said device,
   wherein said associated icon(s) is/are displayed on a first display scene of said user interface, and
   wherein each of said neural stimuli is presented to said user to test for a user response to said neural stimulus;

d) obtaining said user response by monitoring user selection of the associated icon subjectively corresponding to a user-selected neural stimulus; and e) adjusting said neural prosthesis so that the user is enabled to optimally detect said neural stimuli.

These steps are optionally repeated for each of one, some, or many neural stimuli, as for example in a multi-channel neural prosthesis.

In a preferred embodiment, the method comprises the additional step of providing feedback to the user for correct and incorrect responses.

In another aspect of the inventive subject matter, feedback to the user is provided within said first display scene.

In another aspect of the inventive subject matter, feedback to the user is provided within a second display scene.

In another aspect of the inventive subject matter, the test for a response as contemplated by the invention may be a stimulus threshold perception test, a stimulus discrimination test, or a stimulus recognition test. It will be recognized by one of ordinary skill in the art that the exemplary tests listed above are merely representative, and that the inventive methods may incorporate other stimulus-response tests.

In a more preferred embodiment, the test for a response comprises a discrimination test having at least three neural stimuli, wherein at least two of the neural stimuli are identical and at least one neural stimulus is different from the identical neural stimuli.

In another aspect of the inventive subject matter, the neural prosthesis may be selected from the group consisting of a hearing prosthesis, a vision prosthesis, a tactile sensation prosthesis, an olfactory prosthesis, and a gustatory prosthesis. One of ordinary skill in the art will recognize that the methods of the invention may also be adapted to the programming or fitting of other sensorineural prostheses, as well as to the programming or fitting of motor prosthetic devices.

The inventive subject matter incorporates a software program which has a user interface, and which is optionally specially designed for pediatric, teenage, or adult populations. Thus, in another aspect of the inventive subject matter, the steps of presenting neural stimuli to the user, determining user response, and adjusting the neural prosthesis are executed by a computer software program.

The user interface of the invention has two functions. The first function is to test psychophysic parameters that are relevant to the device fitting. In one embodiment of the inventive subject matter, psychophysic testing uses adaptive forced choice parameter procedures that reduce confounding effects of a user's criterion and response bias. Further, the testing part of the software presents commonly used tests of neural perception and grades the user's response, validating the setting of the prosthesis or requiring further fitting. It would be apparent to one of ordinary skill in the art that any or all of these steps may be repeated in order to optimize the setting of the prosthesis.

Thus, in another aspect of the inventive subject matter, for the verification of the adjustment of the neural prosthesis, the inventive subject matter comprises the additional steps of:

presenting a test for neural perception, having correct and incorrect responses for each test stimuli presented to the user;

determining a user response to said test; and analyzing the user response to said test for a correct response by the user.

These steps are optionally repeated for each of one, some, or many neural stimuli presented in a test for neural perception.

In another aspect of the inventive subject matter, the verification component of the software presents neural perception stimuli through a computer system directly to the user's neural prosthesis. User responses are obtained using the computer's graphical user interface and recorded. A variety of neural perception test materials are implemented. Thus, in this preferred embodiment, said neural perception test is presented directly to the user via the neural prosthesis.

A class of sensorineural prosthetic devices are the hearing prostheses. Types of hearing prostheses include simple sound amplification devices such as the traditional hearing aid; more sophisticated sound amplification devices which are adjustable to the specific deficiencies in a user's hearing profile; and implantable devices such as cochlear implants and cortical implants, which bypass the organic hearing mechanism and directly stimulate the sensory nerves and/or brain centers of hearing, to replicate the ability to perceive sound.

Thus, the inventive subject matter additionally relates to a method for user-directed fitting of a hearing prosthesis to a hearing-impaired user, comprising the steps of:

a) connecting a hearing prosthesis to the user;

b) connecting an external device for user-directed fitting of a hearing prosthesis to said hearing prosthesis, for providing a test sound stimulus to said user and receiving a user response;

c) presenting one or more sound stimuli to said user through said hearing prosthesis, each said sound stimulus having an associated icon displayed by a user interface connected to said device,
   wherein each of said sound stimuli is presented to said user to test for a user response to said sound stimulus using a stimulus threshold perception test, a stimulus discrimination test, or a stimulus recognition test;

d) obtaining said user response by monitoring user selection of the associated icon subjectively corresponding to a user-selected sound stimulus; and e) adjusting said hearing prosthesis so that the user is enabled to optimally detect said sound stimuli.

These steps are optionally repeated for each of one, some, or many sound stimuli, as for example in a multi-channel hearing prosthesis.

In one embodiment, the prosthesis may include a sound processor driving a transmitter, a transcutaneous receiver, and an implanted electrode. In a multiple channel system, the signal is applied sequentially to each channel. The dynamic range is optionally identified at each such frequency step to establish the desired aided threshold. Thus, in a more preferred embodiment, said hearing prosthesis comprises a multichannel sound processor, and said steps are carried out for each channel of said sound processor.

In another aspect of the inventive subject matter, the hearing prosthesis may comprise a sound processor driving an implanted electrode. It will be recognized by one of ordinary skill in the art that although external processors and implanted electrodes are the current state-of-the-art technology in neural prosthetic devices for the interface between an external stimulus, the prosthetic device, and the target nervous system tissue, it is expected that any alternate system for transmitting a signal to nerve tissue may be freely interchanged within the inventive methods.

Prosthetic devices have been placed directly in the cochlea or in close proximity to the cochlea for electrical stimulation of the auditory nerve or cochlea are known in the art. Cochlear prostheses produce sensations of sound in deaf patients by direct electrical stimulation of the auditory nerve. In modern, multichannel cochlear prostheses, several different sites are stimulated at various distances along the cochlea to evoke the different pitches of sound perception that are normally encoded by nerve activity originating from the respective sites. The patterns of electrical stimulation are derived from acoustic signals picked up by a microphone and transformed by a speech processor that is programmed to meet the particular requirements of each patient. Thus, in another aspect of the inventive subject matter, a hearing prosthesis as contemplated by the invention is a Cochlear implant.

An implanted cochlear stimulator (ICS) is an electronic device that helps a profoundly deaf patient to achieve the sensation of hearing by applying electrical stimulation directly to the auditory nerve through the cochlea. An ICS includes electronic circuitry, hermetically sealed for implantation, and an electrode array comprising a plurality of spaced-apart, independent, individual electrodes suitable for insertion into the cochlea. An ICS system includes a microphone for sensing audio sounds, a speech processor for processing the sensed audio sounds and converting such to electrical stimulation signals, and a cochlear stimulator for receiving the electrical stimulation signals and directing them to the appropriate electrode or electrodes of the electrode array. Typically, the microphone and speech processor are external components worn or carried by the patient, and the electrical stimulation signals produced by the speech processor are coupled into the implanted cochlear stimulator through an inductive, radio frequency, or other wireless link.

When the ICS is initially implanted in the patient, and during follow-up tests and checkups thereafter, it is necessary to fit the ICS to the patient. Such fitting includes adjustment of the base amplitude or intensity of the various neural stimuli generated by the ICS from the factory settings or default values to values that are most effective and comfortable for the patient. For example, the intensity or amplitude and/or duration of the individual stimulation pulses provided by the ICS must be mapped to an appropriate dynamic audio range so that the appropriate "loudness" of sensed audio signals is perceived. That is, loud sounds should be sensed by the patient at a level that is perceived as loud, but not painfully loud. Soft sounds should similarly be sensed by the patient at a level that is soft, but not so soft that the sounds are not perceived at all.

Fitting and adjusting the intensity of the neural stimuli and other parameters of a cochlear implant to meet a given patient's needs thus requires determining the electrical stimulation threshold levels at which sound is perceived, at which a comfortable sound level is perceived, and the perceptual loudness growth function resolution within the patient's dynamic range. Previously, these psychophysical parameters have been determined by a clinician presenting various neural stimuli to the patient and relying on either subjective feedback from the patient or objective physiological testing to determine, in the clinician's view, how such neural stimuli is perceived. Subjective feedback typically takes the form of either verbal or non-verbal feedback in adult and child patients: "Can you hear that? How about now? How about now? Is this too loud? How about now? How about now?". The inventive subject matter eliminates the need for and the inaccuracy inherent in this questioning process.

Unfortunately, relying on subjective feedback in this manner is difficult, particularly for those patients who may have never heard sound before and/or those who have never heard electrically-generated "sound". For young children, the problem is exacerbated by a short attention span, as well as difficulty in understanding instructions and concepts, such as high and low pitch, softer and louder, same and different. Furthermore, in the developing nervous system of young children and in the accommodating system of adults, frequent changes in the intensity of the neural stimuli may be required for optimal benefit. These changes may require frequent refitting sessions or, ideally, continuous adjustment during use in response to the loudness perceived by the brain. Frequent refitting requires both additional clinician time and more time in the clinic for the patient, and often the patient's family members as well.

One technology-based solution to the problem of effectively fitting a cochlear implant is the monitoring of physiological signals generated by the nervous system to control the level of stimulation that the ICS applies to the cochlea. When neurons are activated by natural or artificial means, they generate action potentials. The current produced by a single neuron is very small, but electrical stimulation, such as is applied by an ICS, tends to recruit large numbers of neurons synchronously. This results in a compound action potential that can be recorded electronically in the tissues surrounding the neurons, particularly in the fluid-filled cochlear ducts where the stimulating electrodes of an ICS are usually located. The amplitude of this compound action potential is approximately related to the number of auditory neurons that have been activated by the electrical stimulation. The level of stimulation at which a compound action potential can first be recorded corresponds approximately to the threshold for hearing, or a small, fixed value above that level.

The action potentials produced by auditory neurons are conducted to various relay nuclei of the brainstem, which transform the information into action potentials that are transmitted by other neurons to yet further nuclei and eventually to the perceptual centers in the cerebral cortex. The compound action potentials resulting from patterns of neural activity in these subsequent nuclei can also be recorded electronically, but they are very much weaker, less accessible, and more variable. Typically, compound action potentials are recorded by widely spaced external electrodes on the scalp and enhanced by stimulus-triggered averaging, in which the small and noisy signals recorded following each of thousands of identical stimuli are added together in order to reduce the effects of noise inherent in the electrodes and amplifiers used to detect the scalp potentials.

Testing for evoked action potentials and adjusting the prosthesis accordingly is one method for objective fitting of the prosthesis. The amplitude of these electrical auditory brainstem responses (hereinafter "EABRs") depends not only on the number of auditory neurons that are initially stimulated, but also on the size and condition of the nuclei, the connections between them, and on descending signals from the perceptual centers that can influence the transformations produced in the relay nuclei. Obtaining and using EABRs to fit an ICS system is tedious and controversial, particularly in children with uncertain developmental status of the brainstem nuclei. This method is only somewhat effective in fitting the prosthesis, as it does not take into consideration the individual, subjective response of the user to the objectively measurable EABRs.

When nerve signals finally arrive in the perceptual centers, they give rise to the conscious perception of sound and its apparent loudness.

Thus, in another embodiment, the inventive subject matter relates to improved techniques for programming a Cochlear implant system. One of the more perplexing problems facing users of Cochlear implant systems, and the clinicians and physicians who implant and adjust such systems, is properly setting the stimulation parameters used by these systems. That is, each Cochlear implant system must be adjusted to fit an individual patient, so that sounds are properly perceived by that patient, and so that sounds are not painfully too loud, nor undetectably too soft, nor otherwise unintelligible by the patient.

This problem is especially difficult because heretofore so much of what is deemed a "proper" setting has been a determination made by the clinician, based on feedback from the patient. However, due to the age, disability, or other limitations of the patient, often the patient is ineffective at accurately communicating to the attending medical personnel what he or she senses through the implant system. Thus, there is a need in the implantable Cochlear stimulation art for techniques, methods and systems for more accurately fitting the implant system to the individual patient.

Further, a totally deaf or severely hearing impaired person presents a special difficulty in fitting a speech processor. The inner ear may be totally non-responsive to sound waves, but the auditory nerve often can be electrically stimulated to transmit signals to the brain. Isoloudness frequency adjustment and dynamic range compression are necessary for the wearer of a cochlear prostheses. Establishing proper sound response characteristics of the auditory nerve in such patients is more critical and difficult than is the auditory response of a less severely impaired person. In the latter case, it is conventional to merely establish frequency response of the hearing device which matches the dynamic range of the patient based on an audiogram or other hearing test. Of course, fine-tuning to the patient's auditory profile is often still required for optimal effectiveness of the hearing prosthesis.

As the art of cochlear stimulation has advanced, both the implanted portion of the cochlear stimulation system and the externally wearable speech processor have become increasingly complicated and sophisticated. The amount of control and discretion exercisable by an audiologist in selecting the modes and methods of operation of the cochlear stimulation system have increased dramatically, and it is no longer possible to fully control and customize the operation of the cochlear stimulation system through the use of, for example, switches located on the speech processor. As a result, it has become necessary to utilize an implantable cochlear stimulator fitting system to establish the appropriate operating modes of the cochlear stimulation system, and then to download such programming into the speech processor.

Unfortunately, currently available systems for programming or fitting of cochlear stimulation systems, while providing a degree of flexibility in the programming of the modes and methods of operation of the cochlear stimulation system based solely or in part of objective measurements taken from the patient, lack the ability to fully integrate subjective patient observations as to the effectiveness of the hearing prosthesis.

Thus, in a preferred embodiment of the inventive subject matter, the method is directed to the fitting of a Cochlear implant.

In another aspect of the inventive subject matter, the test for a response as contemplated by the invention may be a stimulus discrimination test which comprises four sounds, three of which are identical and one of which is different from the three identical sounds. It will be recognized by one of ordinary skill in the art that the exemplary stimulus discrimination test described above is merely representative, and that the inventive methods may incorporate other stimulus discrimination tests.

In a further preferred embodiment, the method of the inventive subject matter additionally comprises the step of providing feedback to the user for correct and incorrect responses.

Another feature of the invention is the use of electrical and visual stimulation to establish the proper fitting response of a patient. In another embodiment, the inventive subject matter incorporates a software program which has a graphical user interface designed for pediatric or adult populations. In this embodiment, the graphical user interface is modeled after a video game based interface. Thus, in another more preferred embodiment, each icon associated with a sound is an animation, said user interface is a graphical user interface, and said feedback is visual feedback displayed by said graphical user interface, wherein said feedback is provided to the user within a plurality of display scenes of said graphical user interface.

In a more preferred embodiment, each said animation is a cartoon character.

As discussed above, the graphical user interface has two functions. The first function is to test psychophysic parameters that are relevant to the device fitting. In one embodiment of the inventive subject matter, psychophysic testing uses adaptive forced choice parameter procedures that reduce confounding effects of a user's criterion and response bias. Further, the testing part of the software presents commonly used speech perception tests and grades the user's response.

Thus, in another aspect of the inventive subject matter, for the verification of the adjustment of the hearing prosthesis, the inventive subject matter additionally comprises the steps of:

presenting a hearing perception test, having correct and incorrect responses for each test stimuli presented to the user;

determining a user response to said hearing perception test; and analyzing the user response to said hearing perception test for a correct response by the user.

These steps are optionally repeated for each of one, some, or many hearing perception test stimuli.

The verification component of the hearing software presents speech perception stimuli through the computer system directly to the user's hearing prosthesis, such as a cochlear implant system. Responses are recorded using the computer's graphical user interface. Standard speech perception test materials, consonant and vowel confusion matrices, and other speech perception tests known in the art are implemented. By feeding the neural stimuli directly to the hearing prosthesis, confounding effects of presentation level, talker, and background noise are eliminated. Thus, in another more preferred embodiment, said hearing perception test is presented directly to the user via the hearing prosthesis.

In a more preferred embodiment, said hearing perception test is selected from the group consisting of standard speech perception tests, and consonant and vowel confusion tests.

The inventive subject matter most particularly relates to a method for user-directed fitting of a hearing prosthesis to a hearing-impaired user, comprising the steps of:

a) connecting a hearing prosthesis to the user;
b) connecting an external device for user-directed fitting of a hearing prosthesis, having a graphical user interface, to said hearing prosthesis for providing a test sound stimulus to said user and receiving a user response;
c) presenting at least three sound stimuli to said user through said hearing prosthesis, each said sound stimulus having an associated animation icon displayed by said graphical user interface,
   wherein at least two of the sound stimuli are identical and at least one sound stimulus is different from the identical sound stimuli;
d) obtaining said user response by monitoring user selection of the associated animation icon subjectively corresponding to a user-selected sound stimulus which differs from the identical sound stimuli;
e) providing visual feedback for correct and incorrect responses, displayed to the user within a plurality of display scenes of said graphical user interface; and
f) adjusting said neural prosthesis so that the user is enabled to optimally detect said differing sound stimulus from the identical sound stimuli,
   wherein the steps of presenting sound stimuli to the user, determining user response, providing visual feedback, and adjusting the hearing prosthesis are executed by a computer software program.

In a preferred embodiment, the method of the inventive subject matter additionally comprises verification of the adjustment of the neural prosthesis by the steps of:
   presenting a hearing perception test, having correct and incorrect responses, directly to the user via the hearing prosthesis;
   determining a user response to said hearing perception test; and
   analyzing the user response to said hearing perception test for a correct response by the user,
      wherein said verification steps are executed by a computer software program.

These steps are optionally repeated for each of one, some, or many hearing perception test stimuli.

The methods of the inventive subject matter are particularly advantageous with totally deaf and severely hearing impaired individuals, but have applicability to other hearing impaired persons requiring a hearing prosthesis.

Additionally, the present invention relates to an apparatus for user-directed fitting of a neural prosthesis to a sensorineural-impaired user, comprising:
a) an input device;
b) a computer processor;
c) a memory device;
d) an information storage and retrieval device;
e) a graphical user interface output device; and
f) a set of computer-readable instructions for processing input and generating output, comprising the steps of:
   i) presenting a neural stimulus to a user through a neural prosthesis, each said neural stimulus having an associated animation icon displayed by said graphical user interface;
   ii) obtaining a user response to said neural stimulus by monitoring user selection of the associated animation icon subjectively corresponding to a user-selected neural stimulus;
   iii) providing visual feedback for correct and incorrect responses, displayed to the user within a plurality of display scenes of said graphical user interface; and
   iv) adjusting said neural prosthesis so that the user is enabled to optimally detect said neural stimulus.

EXAMPLES

The following examples are illustrative of the inventive subject matter and are not intended to be limitations thereon.

Example 1

A PROTOTYPE NEURAL PROSTHESIS FITTING SYSTEM UTILIZING A SOUND DISCRIMINATION TEST

The following example illustrates a cochlear implant fitting system for a totally deaf or severely hearing impaired person. In this example, an engaging environment suitable for a range of ages that only uses sound for experimental purposes has been created. Sound is commonly used to keep the attention of children of all ages. In the inventive subject matter, we must maintain attention with purely visual means. We expect that young children will respond best to simple scenes that do not have reward animations because they would be too distracting. Older children and adults may require increased visual reinforcement. To accomplish this, six exemplary scenes have been developed, with alternate animations freely interchangeable.

For the simplest scenes, which may be most applicable to the youngest children, we have developed a simple shape scene and a balloon scene. Appropriate to the test being administered, the shape or balloon corresponding to a sound is selected by the user and the responses are incorporated into the fitting software. Responses for these scenes do not have visual feedback for correct and incorrect choices. Young children are able to perform adaptive forced choice psychophysical procedures that are not largely influenced by the patient's criterion and bias.

For older children and others who require feedback and scenes of intermediate sophistication, we have developed a frog screen and a cat screen, which have more interesting stimuli. These scenes may optionally have in-scene feedback provided for correct and incorrect responses. For example, in the frog screen, the mouse pointer is depicted as a fly with flapping wings. If a correct frog is chosen, the frog jumps up and eats the fly. If an incorrect frog is chosen, the frog turns its head away from the fly.

Finally, for the individuals with the most demanding attention requirements, we have developed a fishing scene and a Godzilla scene. For a correct or an incorrect response, the screen changes and displays a corresponding short animation for a correct or an incorrect response in a second scene; then user is returned to the test screen. Exemplary screen shots for the six described scenes are shown in FIG. 1.

In an exemplary discrimination test of the inventive subject matter, four tones are presented; each tone is associated with an animation of a cartoon character. The subject indicates which tone, which is always the second or third in our most preferred embodiment, differs from the other three by selecting the appropriate character using the mouse or other computer input device.

Results are saved by the fitting software and an optimized neural stimulation profile is developed for the individual user. Successful programming is possible at a location convenient to the user, without children missing school and/or adults missing work.

Example 2

A PROTOTYPE NEURAL PROSTHESIS FITTING SYSTEM UTILIZING A THRESHOLD PERCEPTION TEST

Utilizing the same general system parameters of Example 1, this example illustrates another embodiment of a cochlear implant fitting system for a totally deaf or severely hearing impaired person. In this case, a threshold perception test is used. Again, several scenes are utilized, in which one or more sounds are presented; each sound is associated with an animation of a cartoon character. The subject indicates either (1) using a single animation, which tone in a series of increasing amplitude is heard, by selecting the character using the mouse or other computer input device when the sound is heard; or (2) which tone in a series of sounds of increasing amplitude are presented, with each tone associated with a separate animation, by selecting the appropriate character using the mouse or other computer input device.

An exemplary single character animation scene is a single groundhog which pops out of each of a series of increasing larger holes; the mouse pointer is depicted as a mallet, and the groundhog is hit when the sound is first detected by the user.

An exemplary multi-character animation scene is a series of increasing larger frogs; as in Example 1, the mouse pointer is depicted as a fly, and the fly is fed to the corresponding frog when the test sound is first detected by the user.

Results are saved by the fitting software and an optimized neural stimulation profile is developed for the individual user. As in Example 1, the exemplary scenes described are freely interchangeable with alternate animation characters and test-type variations.

Example 3

EXEMPLARY SOFTWARE

In another non-limiting example, which is the current best mode of the inventive subject matter, the animation software has been written in the Lingo programming language, a programming language commonly used in commercial software and website programming. Adaptive procedures are implemented in C++. Stimuli are called using ActiveX. The use of ActiveX stimulus calls will allow easy transition to cochlear implant function calls, as the research interface to some major commercial interfaces uses ActiveX, and other manufacturers have wrapped an ActiveX shell around their existing implant communicator C code. However, as one of ordinary skill in the art will readily understand, the choice of software programming language and similar characteristics is one of convenience in integrating the product into existing systems. The exemplary programming languages and interfaces are optionally replaced with other programming languages and interfaces known in the art.

Example 4

FITTING OF A VISION PROSTHESIS

A vision-impaired patient presents for programming of a vision prosthesis. A method of the inventive subject matter is used to optimally program the prosthesis, providing the patient with superior effectiveness of the prosthesis for the recognition of persons and environmental objects, and enhanced quality of life.

Example 5

FITTING OF A CONVENTIONAL HEARING PROSTHESIS

A hearing-impaired patient, who is not totally deaf or severely hearing impaired, presents for fitting of a programmable hearing aid. A method of the inventive subject matter is used to optimally program the hearing aid, providing the patient with superior effectiveness of the prosthesis for the recognition of speech and environmental sounds, and enhanced quality of life.

The invention being thus described, it will be obvious that the same may be modified or varied in many ways. Such modifications and variations are not to be regarded as a departure from the spirit and scope of the invention and all such modifications and variations are intended to be included within the scope of the following claims.

I claim:

1. A method for user-directed fitting of a neural prosthesis to a sensorineural-impaired user, comprising the steps of:
    a) connecting a neural prosthesis to the user;
    b) connecting an external device for user-directed fitting of a neural prosthesis to said neural prosthesis, for providing a test neural stimulus to said user and receiving a user response;
    c) presenting one or more neural stimuli to said user through said neural prosthesis, each said neural stimulus having an associated icon displayed by a user interface connected to said device,
        wherein said associated icon(s) is/are displayed on a first display scene of said user interface, and
        wherein each of said neural stimuli is presented to said user to test for a user response to said neural stimulus;
    d) obtaining said user response by monitoring user selection of the associated icon subjectively corresponding to a user-selected neural stimulus; and
    e) adjusting said neural prosthesis so that the user is enabled to optimally detect said neural stimuli.

2. The method of claim 1, comprising the additional step of providing feedback to the user for correct and incorrect responses.

3. The method of claim 2, wherein said feedback to the user is provided within said first display scene.

4. The method of claim 2, wherein said feedback to the user is provided within a second display scene.

5. The method of claim 1, wherein said test for a response is selected from the group consisting of a stimulus threshold perception test, a stimulus discrimination test, and a stimulus recognition test.

6. The method of claim 1, wherein said test comprises a discrimination test having at least three neural stimuli, wherein at least two of the neural stimuli are identical and at least one neural stimulus is different from the identical neural stimuli.

7. The method of claim 1, wherein said neural prosthesis is selected from the group consisting of a hearing prosthesis, a vision prosthesis, a tactile sensation prosthesis, an olfactory prosthesis, and a gustatory prosthesis.

8. The method of claim 1, wherein the steps of presenting neural stimuli to the user, determining user response, and adjusting the neural prosthesis are executed by a computer software program.

9. The method of claim 1, additionally comprising verification of the adjustment of the neural prosthesis by the steps of:
    presenting a test for neural perception, having correct and incorrect responses for each test stimuli presented to the user;
    determining a user response to said test; and
    analyzing the user response to said test for a correct response by the user.

10. The method of claim 9, wherein said neural perception test is presented directly to the user via the neural prosthesis.

11. A method for user-directed fitting of a hearing prosthesis to a hearing-impaired user, comprising the steps of:
- a) connecting a hearing prosthesis to the user;
- b) connecting an external device for user-directed fitting of a hearing prosthesis to said hearing prosthesis, for providing a test sound stimulus to said user and receiving a user response;
- c) presenting one or more sound stimuli to said user through said hearing prosthesis, each said sound stimulus having an associated icon displayed by a user interface connected to said device,
   - wherein each of said sound stimuli is presented to said user to test for a user response to said sound stimulus using a stimulus threshold perception test, a stimulus discrimination test, or a stimulus recognition test;
- d) obtaining said user response by monitoring user selection of the associated icon subjectively corresponding to a user-selected sound stimulus; and
- e) adjusting said hearing prosthesis so that the user is enabled to optimally detect said sound stimuli.

12. The method of claim 11, wherein said hearing prosthesis comprises a multichannel sound processor, and said steps are carried out for each channel of said sound processor.

13. The method of claim 11, wherein said hearing prosthesis comprises a sound processor driving an implanted electrode.

14. The method of claim 11, wherein said hearing prosthesis is a Cochlear implant.

15. The method of claim 11, wherein said test for a response is a stimulus discrimination test which comprises four sounds, three of which are identical and one of which is different from the three identical sounds.

16. The method of claim 11, comprising the additional step of providing feedback to the user for correct and incorrect responses.

17. The method of claim 16, wherein each said associated icon is an animation, said user interface is a graphical user interface, and said feedback is visual feedback displayed by said graphical user interface,
   - wherein said feedback is provided to the user within a plurality of display scenes of said graphical user interface.

18. The method of claim 17, wherein each said animation is a cartoon character.

19. The method of claim 11, additionally comprising verification of the adjustment of the hearing prosthesis by the steps of:
   - presenting a hearing perception test, having correct and incorrect responses for each test stimuli presented to the user;
   - determining a user response to said hearing perception test; and
   - analyzing the user response to said hearing perception test for a correct response by the user.

20. The method of claim 19, wherein said hearing perception test is presented directly to the user via the hearing prosthesis.

21. The method of claim 19, wherein said hearing perception test is selected from the group consisting of standard speech perception tests, and consonant and vowel confusion tests.

22. A method for user-directed fitting of a hearing prosthesis to a hearing-impaired user, comprising the steps of:
- a) connecting a hearing prosthesis to the user;
- b) connecting an external device for user-directed fitting of a hearing prosthesis, having a graphical user interface, to said hearing prosthesis for providing a test sound stimulus to said user and receiving a user response;
- c) presenting at least three sound stimuli to said user through said hearing prosthesis, each said sound stimulus having an associated animation icon displayed by said graphical user interface,
   - wherein at least two of the sound stimuli are identical and at least one sound stimulus is different from the identical sound stimuli;
- d) obtaining said user response by monitoring user selection of the associated animation icon subjectively corresponding to a user-selected sound stimulus which differs from the identical sound stimuli;
- e) providing visual feedback for correct and incorrect responses, displayed to the user within a plurality of display scenes of said graphical user interface; and
- f) adjusting said neural prosthesis so that the user is enabled to optimally detect said differing sound stimulus from the identical sound stimuli,
   - wherein the steps of presenting sound stimuli to the user, determining user response, providing visual feedback, and adjusting the hearing prosthesis are executed by a computer software program.

23. The method of claim 22, additionally comprising verification of the adjustment of the neural prosthesis by the steps of:
   - presenting a hearing perception test, having correct and incorrect responses, directly to the user via the hearing prosthesis;
   - determining a user response to said hearing perception test; and
   - analyzing the user response to said hearing perception test for a correct response by the user,
     - wherein said verification steps are executed by a computer software program.

24. An apparatus for user-directed fitting of a neural prosthesis to a sensorineural-impaired user, comprising:
- a) an input device;
- b) a computer processor;
- c) a memory device;
- d) an information storage and retrieval device;
- e) a graphical user interface output device; and
- f) a set of computer-readable instructions for processing input and generating output, comprising the steps of:
   - i) presenting a neural stimulus to a user through a neural prosthesis, each said neural stimulus having an associated animation icon displayed by said graphical user interface;
   - ii) obtaining a user response to said neural stimulus by monitoring user selection of the associated animation icon subjectively corresponding to a user-selected neural stimulus;
   - iii) providing visual feedback for correct and incorrect responses, displayed to the user within a plurality of display scenes of said graphical -user interface; and
   - iv) adjusting said neural prosthesis so that the user is enabled to optimally detect said neural stimulus.

* * * * *